(12) United States Patent
Qian et al.

(10) Patent No.: US 12,427,032 B2
(45) Date of Patent: Sep. 30, 2025

(54) BIONIC INTER VERTEBRAL DISC WITH MECHANICAL ANISOTROPY

(71) Applicant: JILIN UNIVERSITY, Changchun (CN)

(72) Inventors: Zhihui Qian, Changchun (CN); Weiguo Fan, Changchun (CN); Lei Ren, Changchun (CN); Kunyang Wang, Changchun (CN); Shengli Wang, Changchun (CN); Guangsheng Song, Changchun (CN); Xia Xie, Changchun (CN); Luquan Ren, Changchun (CN)

(73) Assignee: JILIN UNIVERSITY, Changchun (CN)

( * ) Notice: Subject to any disclaimer, the term of this patent is extended or adjusted under 35 U.S.C. 154(b) by 223 days.

(21) Appl. No.: 18/451,189

(22) Filed: Aug. 17, 2023

(65) Prior Publication Data

US 2024/0216146 A1 Jul. 4, 2024

(30) Foreign Application Priority Data

Jan. 3, 2023 (CN) .......................... 202310000888.8

(51) Int. Cl.
*A61F 2/44* (2006.01)

(52) U.S. Cl.
CPC .............. *A61F 2/442* (2013.01); *A61F 2/441* (2013.01); *A61F 2002/444* (2013.01); *A61F 2250/0014* (2013.01)

(58) Field of Classification Search
CPC .......... A61F 2/44–447; A61F 2002/444; A61F 2250/0014
See application file for complete search history.

(56) References Cited

U.S. PATENT DOCUMENTS

| | | | | |
|---|---|---|---|---|
| 11,992,407 B1* | 5/2024 | Qian | ....................... | G06T 17/00 |
| 2007/0225810 A1* | 9/2007 | Colleran | ............... | A61F 2/4465 |
| | | | | 623/17.13 |
| 2009/0222098 A1* | 9/2009 | Trieu | ..................... | A61F 2/442 |
| | | | | 623/17.12 |
| 2013/0066427 A1* | 3/2013 | Liu | ..................... | C04B 35/6365 |
| | | | | 623/23.61 |

FOREIGN PATENT DOCUMENTS

| | | | |
|---|---|---|---|
| CN | 103190969 A | * | 7/2013 |
| CN | 113017936 A | * | 6/2021 |

* cited by examiner

*Primary Examiner* — Nicholas J Plionis
(74) *Attorney, Agent, or Firm* — BROOKS KUSHMAN P.C.

(57) ABSTRACT

A bionic intervertebral disc with mechanical anisotropy includes an upper end plate, a core and a lower end plate. The core includes outer fibrous rings, a middle transition zone and an inner nucleus pulposus. The fibrous rings comprise collagen fiber sheets and collagen fibers, each of the collagen fibers is attached to a surface of a corresponding one of the collagen fiber sheets and arranged at an inclination angle, ones of the collagen fibers which are on every two adjacent layers of the collagen fiber sheets are arranged crosswise with each other. A honeycomb meshing size of a portion, which is located at a fibrous-ring transition zone, of the honeycomb structure is smaller and more compact, and a honeycomb meshing size of a portion, which is located at a nucleus pulposus transition zone, of the honeycomb structure is larger and sparser.

4 Claims, 2 Drawing Sheets

BIONIC INTER VERTEBRAL DISC WITH MECHANICAL ANISOTROPY

CROSS-REFERENCE TO RELATED APPLICATION

This application claims foreign priority benefits under 35 U.S.C. § 119(a)-(d) to Chinese Patent Application No. 202310000888.8 filed on Jan. 3, 2023, which is hereby incorporated herein by reference in its entirety.

TECHNICAL FIELD

The present disclosure relates to a bionic intervertebral disc with mechanical anisotropy, and belongs to the technical field of implantable devices.

BACKGROUND

Degenerative intervertebral disc disease is a common and frequently-occurring disease of human beings. There are two main treatment methods of traditional treatment and surgical treatment. The treatment method of traditional treatment includes physical therapy and drug therapy, and the treatment method of surgical treatment includes fusion and replacement. For mild patients, the physical therapy or the traditional drug therapy is mainly adopted. However, the traditional treatment can only relieve pain symptoms but the disease cannot be completely cured, so that the surgical treatment has gradually become the first choice for patients when the traditional treatment has been adopted and the effect is not satisfactory.

Fusion has the characteristics of maintaining the intervertebral height and improving the pains of patients, but fusion can lose the movement function of vertebral segments and accelerate the degenerative diseases of adjacent vertebral segments. However, total disc replacement not only retains the movement range of the vertebral segments, but also significantly reduces the risk of degeneration of adjacent segments, so that the shortcomings of fusion are effectively solved. Therefore, total disc replacement becomes a more advanced and effective treatment scheme. At present, there are two types of artificial intervertebral discs commonly used in the world: a ball-and-socket joint type and a one-piece type. Almost all artificial intervertebral discs adopt isotropic structural design or homogeneous materials, so that the mechanical properties have no difference in all directions. As a result, the movement range of the vertebral segment where the intervertebral disc prosthesis is implanted cannot be matched with the physiological movement, which results in abnormal intervertebral movement and load transmission disorder, and even results in problems such as sinking and dislocation of the artificial intervertebral disc prosthesis. In the disclosed patent of a bionic intervertebral disc with variable stiffness, the variable stiffness of the structure of the bionic intervertebral disc can be realized mainly by adjusting the elastic modulus of collagen fibers, so that the bionic intervertebral disc has the functional characteristics similar to the anisotropic stiffness of the biological intervertebral disc to some extent. But, the change of the inclination angle of the collagen fibers in different areas of the fibrous ring of the biological intervertebral disc and the structural and material characteristics of the transition zone are not considered. Biomechanical research shows that the change of the inclination angle of the collagen fibers of the fibrous ring in different areas of the biological intervertebral disc seriously affects the stress of the fibrous ring, and then affects the overall mechanical anisotropy of the intervertebral disc. At the same time, the transition zone, as the only connecting area between the nucleus pulposus and the fibrous ring, also plays an important role in mechanical regulation, especially under low loads. The structural characteristics and material properties of the nucleus pulposus and the fibrous ring are very important for the mechanical performance of the intervertebral disc. It can be seen that the human biological intervertebral disc has excellent mechanical anisotropy due to the fine structure and material properties of the fibrous ring and the transition zone, so that different physiological movement modes are achieved. However, the current artificial intervertebral disc cannot reproduce the characteristic of the excellent mechanical anisotropy, which results in a series of adverse clinical problems after implantation of the bionic intervertebral disc in human body. Therefore, it is urgent to develop a bionic intervertebral disc with mechanical anisotropy.

SUMMARY

In order to solve the technical problems existing in the existing artificial intervertebral disc, the present disclosure provides a bionic intervertebral disc with mechanical anisotropy. The bionic intervertebral disc has the structural characteristics and material attributes similar to the human biological intervertebral disc, and can reproduce the mechanical anisotropy characteristic of the human biological intervertebral disc, so that the bionic intervertebral disc can be matched with the physiological movement of the vertebrae more naturally after implantation of the bionic intervertebral disc.

In order to achieve the above purpose, some embodiments adopt the following technical solutions.

According to the structural characteristics and material properties of the human biological intervertebral disc, the human biological intervertebral disc includes outer fibrous rings, a middle transition zone and an inner nucleus pulposus. The fibrous ring includes collagen fiber sheets and collagen fibers. The collagen fibers are attached to the surface of the collagen fiber sheet and provided with inclination angles. The collagen fibers on adjacent collagen fiber sheets are arranged crosswise with each other. Each of the inclination angles is an included angle between a corresponding one of the collagen fibers and a horizontal plane. An anterior inclination angle of the inclination angles at the anterior part is 20 degrees, and a posterior inclination angle of the inclination angles at the posterior part is 70 degrees. The inclination angles of the collagen fibers are increased in turn from anterior to posterior, and the inclination angles of the collagen fiber on the right side and the left side of the sagittal plane of the bionic intervertebral disc are symmetrically distributed. The transition zone includes a matrix layer and elastic fibers. The elastic fibers are attached to the surface of the matrix layer. The elastic fibers include coarse elastic fibers and fine elastic fibers. The elastic fibers and the matrix layer form a honeycomb structure. The honeycomb structure is smaller in a honeycomb meshing size of a portion of the transition zone opposite to the nucleus pulposus and more compact, and larger in the honeycomb meshing size of a portion of the transition zone opposite to the fibrous rings and sparser. The elastic fibers located in an anterior part of the bionic intervertebral disc are larger in diameter than those located in a posterior part of the bionic intervertebral disc, the fine elastic fibers are interspersed among the coarse elastic fibers. In the process of vertebral movement, the nucleus pulposus in the biological intervertebral disc is compressed to produce deformation and expansion. The honeycomb-shaped elastic fibers and fibrous rings in the transition zone surrounding the nucleus pulposus are successively squeezed. The honeycomb-shaped elastic fibers and fibrous rings in the transition zone limit the deformation and expansion of the nucleus pulposus through tensile forces. However, due to the different tensile forces of the elastic fibers and the collagen fibers in different areas and the different inclination angles of the collagen fibers at different positions of the collagen fiber sheets, the difference of the tensile forces at different positions of the intervertebral disc is further amplified when the expansion of the nucleus pulposus is limited, so that the deformations at different positions of the intervertebral disc are different, and the biological intervertebral disc has the function of mechanical anisotropy.

Based on the structural and material characteristics of the human biological intervertebral disc, the bionic intervertebral disc with mechanical anisotropy includes an upper end plate, a core and a lower end plate. An upper end of the core is fixed on a lower surface of the upper end plate, and a lower end of the core is fixed on an upper surface of the lower end plate. An upper surface of the upper end plate is provided with spikes on the upper end plate, and a lower surface of the lower end plate is provided with lower spikes. The upper and lower spikes play a good role in initial fixation after implantation of the bionic intervertebral disc.

The core includes outer fibrous rings, a middle transition zone and an inner nucleus pulposus. The fibrous ring is composed of a collagen fiber sheet and collagen fibers. The collagen fibers are attached to the surface of the collagen fiber sheet and provided with inclination angles. The adjacent lamellae are arranged crosswise with each other. Upper ends of the collagen fibers are tightly connected with the upper end plate, and lower ends of the collagen fibers are tightly connected with the lower end plate.

The transition zone includes a matrix layer and elastic fibers. The elastic fibers are attached to the surface of the matrix layer. The elastic fibers are composed of coarse elastic fibers and fine elastic fibers.

The elastic fibers and the matrix layer in the transition zone form a honeycomb structure, and the structure is smaller in the honeycomb meshing size of a portion of the transition zone opposite to the nucleus pulposus and more compact, and larger in the honeycomb meshing size of a portion of the transition zone opposite to the fibrous rings and sparser. The elastic fibers located in the intervertebral disc anterior part are larger in diameter than those located in the intervertebral disc posterior part. The intervertebral disc anterior part can bear larger tensile force compared with the intervertebral disc posterior part. The fine elastic fibers are interspersed among the coarse elastic fibers. The fine elastic fibers play a main role under low loads. Heterogeneous materials of the elastic fibers in a softer layer of the transition zone can effectively reduce the stress gradient of the bionic intervertebral disc from the outside to the inside.

The collagen fibers are made of polymer materials with different elastic moduli, the elastic moduli from an intervertebral disc anterior part to an intervertebral disc posterior part are gradiently changed and gradually decreased, and the elastic moduli of the collagen fibers on both sides of a sagittal plane of the bionic intervertebral disc are symmetrically distributed. Because the elastic moduli of the collagen fibers at different positions of each fibrous ring are different, the fibrous rings at different positions are different in tensile forces when the nucleus pulposus is restricted from expanding, thus realizing the anisotropy of the mechanical properties of the intervertebral disc, and the external morphology shows that the deformation degrees of the intervertebral discs at different positions are different, and then the bionic intervertebral disc is matched with the physiological movement of the vertebrae more naturally after implantation.

The fibrous rings include odd-numbered-layer fibrous rings and even-numbered-layer fibrous rings. The number of the collagen fiber sheets is 4 to 25. The collagen fiber sheets include collagen fiber sheet of odd-numbered-layer fibrous rings and collagen fiber sheet of even-numbered-layer fibrous rings.

The odd-numbered-layer fibrous ring includes a collagen fiber sheet of odd-numbered-layer fibrous ring and collagen fiber of odd-numbered-layer fibrous rings. The collagen fiber of odd-numbered-layer fibrous rings are inclined counterclockwise from the bottom end to the upper end on the right side of the sagittal plane, and the collagen fiber of odd-numbered-layer fibrous rings are inclined clockwise from the bottom end to the upper end on the left side of the sagittal plane.

The even-numbered-layer fibrous ring includes a collagen fiber of even-numbered-layer fibrous ring sheet and collagen fiber of even-numbered-layer fibrous rings. The collagen fiber of even-numbered-layer fibrous rings are inclined clockwise from the bottom end to the upper end on the right side of the sagittal plane, and the collagen fiber of even-numbered-layer fibrous rings are inclined counterclockwise from the bottom end to the upper end on the left side of the sagittal plane.

The inclination angle is an included angle between the collagen fibers and a horizontal plane. An anterior inclination angle of the bionic intervertebral disc is 20 degrees, and a posterior inclination angle of the bionic intervertebral disc is 70 degrees. The inclination angle is increased in turn from anterior to posterior, and the inclination angles on both sides of the sagittal plane of the bionic intervertebral disc are symmetrically distributed. The collagen fibers at different positions of the collagen fiber sheets are different in the inclination angles and different in tensile forces when the nucleus pulposus is restricted from expanding, thus realizing the anisotropy of the mechanical properties of the intervertebral disc. During forward flexing (there is no other coupling motion in ideal states), the tensile force $F_{posterior\ collagen\ fibers}$ of the collagen fibers of the odd-numbered-layer fibrous ring of the intervertebral disc posterior part along the longitudinal direction of the collagen fiber is a product of the tensile force $F_{posterior}$ of the collagen fibers on the vertical horizontal plane and the sine of the inclination angle $\alpha$ of the collagen fibers, namely $F_{posterior\ collagen\ fibers}$ is equal to $F_{posterior}$ multiplied by $\alpha°$. The tensile force $F_{posterior\ collagen\ fibers}$ of the collagen fibers of the even-numbered-layer fibrous ring of the intervertebral disc posterior part along the longitudinal direction of the collagen fiber is a product of the tensile force $F_{posterior}$ of the collagen fibers on the vertical horizontal plane and the sine of the inclination angle $\alpha$ of the collagen fibers, namely $F_{posterior\ collagen\ fibers}$ is equal to $F_{posterior}$ multiplied by $\alpha°$. The tensile force of the collagen fibers of the odd-numbered-layer fibrous ring along the longitudinal direction of the collagen fiber is consistent with that of the collagen fibers of the even-numbered-layer fibrous ring along the longitudinal direction of the collagen fiber, represented by $F_{posterior\ collagen\ fibers}$; and the tensile force $F_{posterior}$ on the vertical horizontal plane is the joint moment $M_{posterior}$ of the intervertebral disc posterior part divided by the force arm (the anterior-and-posterior distance of the intervertebral disc is represented by D). During backward extending (there is no other coupling motion in ideal states), the tensile force $F_{anterior\ collagen\ fibers}$ of the collagen fibers of the odd-numbered-layer fibrous ring of the intervertebral disc anterior part along the longitudinal direction of the collagen fiber is a product of the tensile force $F_{anterior}$ of the collagen fibers on the vertical horizontal plane and the sine of the inclination angle $\alpha$ of the collagen fibers, namely $F_{anterior}$ collagen fibers is equal to $F_{anterior}$ multiplied by $\alpha°$. The tensile force $F_{anterior\ collagen\ fibers}$ of the collagen fibers of the even-numbered-layer fibrous ring of the intervertebral disc anterior part along the longitudinal direction of the collagen fiber is a product of the tensile force $F_{anterior}$ of the collagen fibers which is perpendicular to horizontal plane and the sine of the inclination angle $\alpha$ of the collagen fibers, namely $F_{anterior\ collagen\ fibers}$ is equal to $F_{anterior}$ multiplied by $\alpha°$. The tensile force of the collagen fibers of the odd-numbered-layer fibrous ring along the longitudinal direction of the collagen fiber is consistent with that of the collagen fibers of the even-numbered-layer fibrous ring along the longitudinal direction of the collagen fiber, represented by $F_{anterior\ collagen\ fibers}$, and the tensile force $F_{anterior}$ which is perpendicular to horizontal plane is the joint moment $M_{anterior}$ of the intervertebral disc anterior part divided by the force arm (the anterior-and-anterior distance of the intervertebral disc is represented by D). Literature research shows that the joint moment $M_{anterior}$ of the intervertebral disc anterior part is approximately equal to the joint moment $M_{posterior}$ of the intervertebral disc posterior part, represented by M. Therefore, in the forward flexing and backward extending states, the tensile force F of the fibrous ring collagen fibers of the intervertebral disc anterior part and the intervertebral disc posterior part along the longitudinal direction of the collagen fiber can be represented that F is equal to M/D sin $\alpha°$. The inclination angle of the intervertebral disc anterior part 9 is 20 degrees, and the inclination angle of the intervertebral disc posterior part is 70 degrees. The tensile force $F_{anterior}$ of the fibrous ring collagen fibers of the intervertebral disc anterior part along the longitudinal direction of the collagen fiber is equal to M/D sin 20°, and the tensile force $F_{posterior}$ of the fibrous ring collagen fibers of the intervertebral disc posterior part along the longitudinal direction of the collagen fiber is equal to M/D sin 70°. Therefore, $F_{anterior}$ is less than $F_{posterior}$, namely the movement range of forward flexing is greater than the movement range of backward extending, and the data is consistent with the movement range data of a cadaver test. Similarly, in the ideal state of pure lateral bending, the inclination angles on the left and right sides are equal, and the tensile forces of the fibrous ring collagen fibers on both sides of the intervertebral disc are equal, so the movement ranges of left lateral bending and right lateral bending in the cadaver test are basically equal. Similarly, the inclination angles of the fibrous ring collagen fibers in different regions of the intervertebral disc are different, so the tensile forces of the fibrous ring collagen fibers along the longitudinal direction of the collagen fiber is different, thus regulating the mechanical anisotropy in different regions of the intervertebral disc.

The nucleus pulposus is D-shaped, and the stress area of the nucleus pulposus can be increased, so that the stress is more uniform, and local stress concentration is avoided. The upper end plate, the lower end plate and the core are D-shaped, and the shape accords with the appearance characteristics of the human biological intervertebral disc, so that the integral stress is more uniform, and the supporting effect is better.

The surface of the upper end plate is provided with an upper coating, the surface of the lower end plate is provided with a lower coating, and the surfaces of the spikes on upper end plate and the lower spikes are also provided with coatings. The above coatings are all made of hydroxyapatite, undifferentiated mesenchymal cells can be induced to be differentiated into osteoblasts because of affinity interaction to bone tissues, and then the purpose of secondary fixation of the intervertebral disc is achieved.

The upper end plate, the lower end plate, the spikes on upper end plate and the lower spikes are made of polyether ether ketone polymers. The materials are high in hardness, and the problem of prosthesis sinking caused by end plate fractures can be avoided.

The nucleus pulposus is made of an agarose hydrogel analogue. The stiffness can be adjusted by changing the ratio of a base material to a curing agent, and appropriate load response can be produced by the ratio of 10:1.

The collagen fiber sheets are made of a polyurethane polymer material, and the collagen fibers are made of a polyurethane polymer material.

The matrix layer is made of a polyurethane polymer material.

The elastic fibers are made of a polyurethane polymer material.

Compared with the prior art, some embodiments have the following beneficial effects.

Firstly, the mechanical properties of different areas of the bionic intervertebral disc are regulated by the difference of the inclination angles of the collagen fibers at different positions of the bionic intervertebral disc so that the anisotropy of the mechanical properties of the intervertebral disc is realized, and then the bionic intervertebral disc is matched with the physiological movement of the vertebrae more naturally after implantation of the bionic intervertebral disc.

Secondly, heterogeneous materials of the honeycomb-shaped structure of the elastic fiber in the transition zone can effectively reduce the stress gradient of the bionic intervertebral disc from the outside to the inside, so that the heterogeneous materials have better mechanical performances under low loads and play important roles in mechanical anisotropy.

Thirdly, the mechanical properties of different areas of the bionic intervertebral disc are regulated by the combined action of the elastic moduli and the inclination angles of the collagen fibers at different positions of the bionic intervertebral disc, so that the anisotropy of the mechanical properties of the bionic intervertebral disc is realized, and then the bionic intervertebral disc is matched with the physiological movement of the vertebrae more naturally after implantation of the bionic intervertebral disc.

REFERENCE SIGNS 1 upper spike tooth; 2 upper coating; 3 upper end plate; 4 core; 5 collagen fiber; 6 lower end plate; 7 lower coating; 8 lower spike tooth; 9 anterior part of the bionic intervertebral disc; 10 odd-numbered-layer fibrous ring; 11 even-numbered-layer fibrous ring; 12 collagen fiber sheet; 13 fibrous-ring transition zone; 14 transition zone; 15 nucleus pulposus transition zone; 16 nucleus pulposus; 17 posterior part of the bionic intervertebral disc; 18 left side of sagittal plane; 19 sagittal plane of the bionic intervertebral disc; 20 right side of sagittal plane; 21 posterior inclination angle 70°; 22 anterior inclination angle 20°; 23 inclination angle; 24 fibrous ring; 25 matrix layer; 26 elastic fiber; 27 honeycomb structure; 28 horizontal plane; 29 collagen fiber sheet of odd-numbered-layer fibrous ring; 30 collagen fiber sheet of even-numbered-layer fibrous ring; 31 collagen fiber of odd-numbered-layer fibrous ring; 32 collagen fiber of even-numbered-layer fibrous ring.

DETAILED DESCRIPTION

Figure 1:
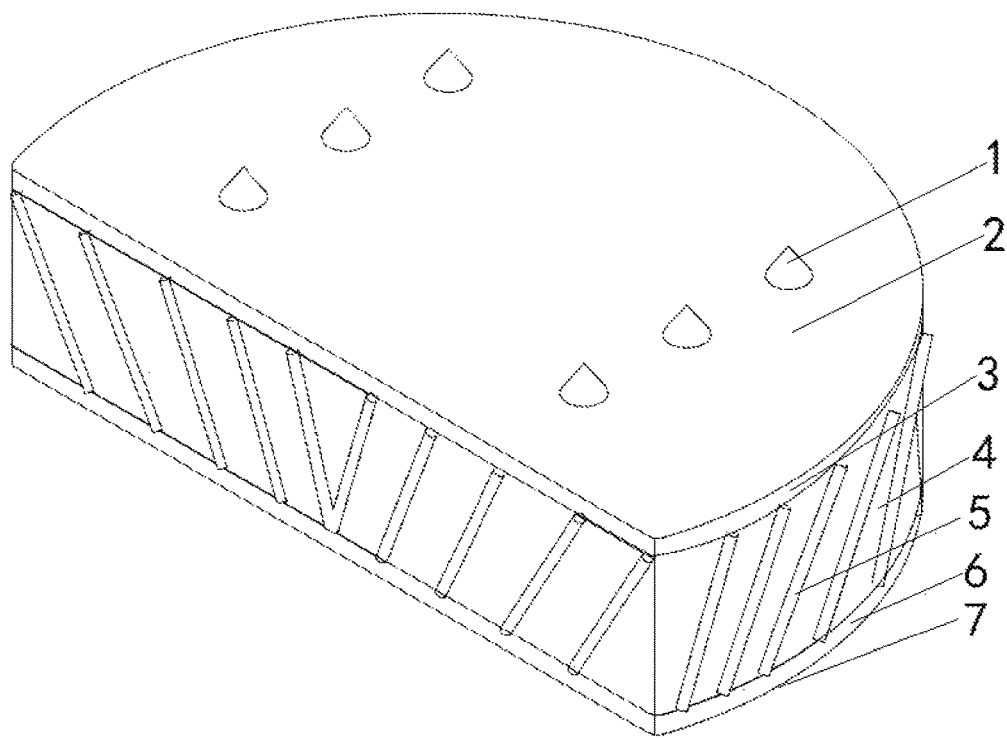
FIG. 1 is a perspective structural schematic diagram of a bionic intervertebral disc with mechanical anisotropy according to an embodiment of the present disclosure.
Figure 2:
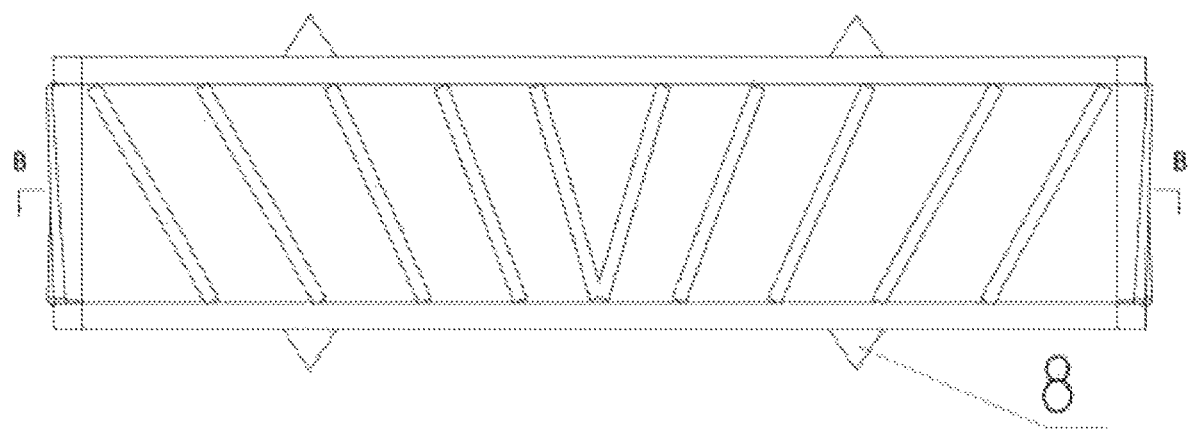
FIG. 2 is a front view of a bionic intervertebral disc with mechanical anisotropy according to an embodiment of the present disclosure.
Figure 3:
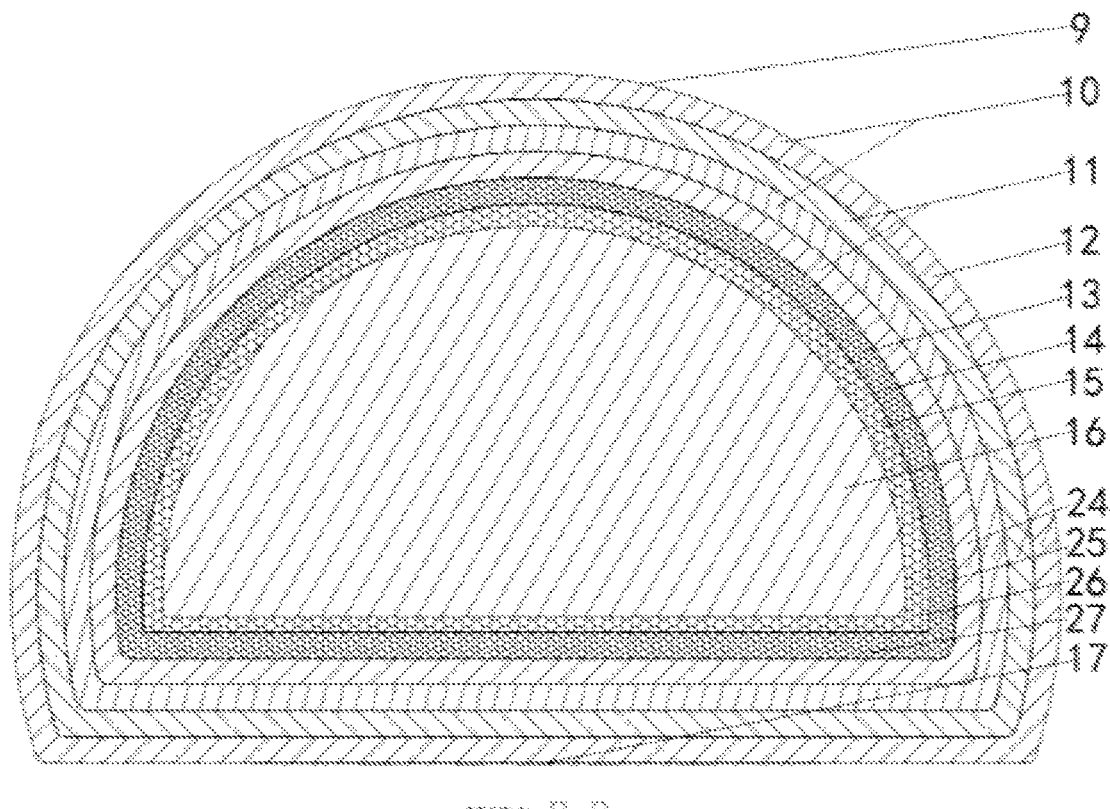
FIG. 3 is a section view along line B-B of the bionic intervertebral disc with mechanical anisotropy shown in FIG. 2.
Figure 4:
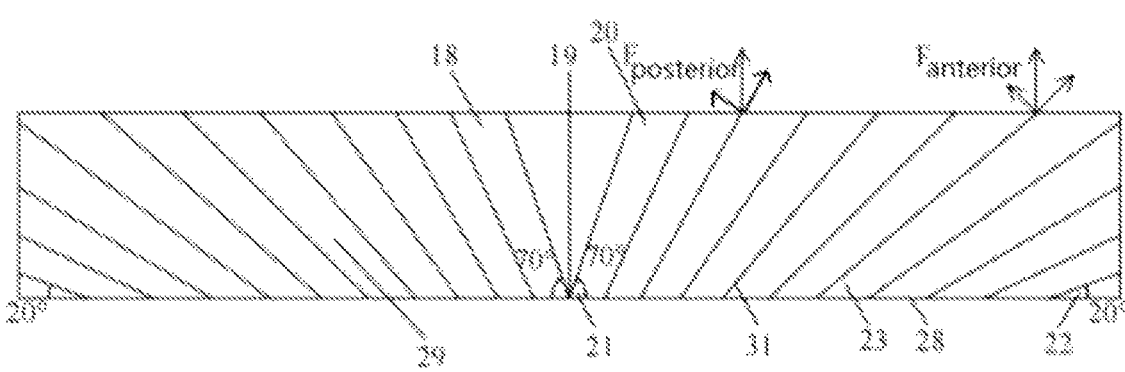
FIG. 4 is an unfolded structural schematic diagram of an annular collagen fiber sheet of odd-numbered-layer fibrous ring.
Figure 5:
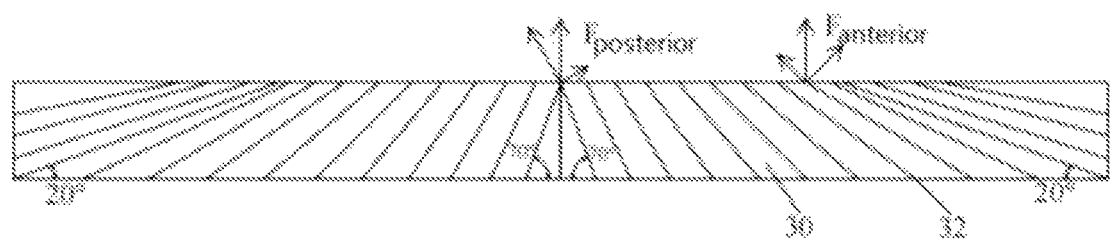
FIG. 5 is an unfolded structural schematic diagram of an annular collagen fiber sheet of even-numbered-layer fibrous ring.

Referring to FIG. 1 to FIG. 5, a bionic intervertebral disc with mechanical anisotropy includes an upper end plate 3, a core 4 and a lower end plate 6. An upper end of the core 4 is fixed on a lower surface of the upper end plate 3, and a lower end of the core 4 is fixed on an upper surface of the lower end plate 6. An upper surface of the upper end plate 3 is provided with upper spikes 1, and a lower surface of the lower end plate 6 is provided with lower spikes 8.

The core 4 includes outer fibrous rings 24, a middle transition zone 14 and an inner nucleus pulposus 16. The fibrous ring 24 includes collagen fiber sheets 12 and collagen fibers 5. The collagen fibers 5 are each attached to the surface of a corresponding collagen fiber sheet 12 and arranged at an inclination angle 23. The collagen fibers 5 on every two adjacent collagen fiber sheets are arranged crosswise with each other. Upper ends of the collagen fibers 5 are tightly connected with the upper end plate 3, and lower ends of the collagen fibers 5 are tightly connected with the lower end plate 6.

The transition zone 14 includes a matrix layer 25 and elastic fibers 26. The elastic fibers 26 are attached to the surface of the matrix layer 25. The elastic fibers 26 include coarse elastic fibers and fine elastic fibers.

The elastic fibers 26 and the matrix layer 25 of the transition zone 14 form a honeycomb structure 27. A honeycomb meshing size of a portion, which is located at the fibrous-ring transition zone 13, of the honeycomb structure 27 is smaller and more compact. A honeycomb meshing size of a portion, which is located at the nucleus pulposus transition zone 15, of the honeycomb structure 27 is larger and sparser. The elastic fibers 26 located in an anterior part 9 of the bionic intervertebral disc are larger in diameter than those located in a posterior part 17 of the bionic intervertebral disc, the fine elastic fibers are interspersed among the coarse elastic fibers, and the fine elastic fibers play a main role under low loads. Heterogeneous materials of the elastic fibers 26 in a softer layer of the transition zone 14 can effectively reduce the stress gradient of the bionic intervertebral disc from the outside to the inside.

The collagen fibers 5 are made of polymer materials with different elastic moduli, the elastic moduli of the collagen fibers from the anterior part 9 to the posterior part 17 are gradiently changed and gradually decreased, and the elastic moduli of the collagen fibers 5 on right side and left side of an sagittal plane 19 of the bionic intervertebral disc are symmetrically distributed. Because the elastic moduli of the collagen fibers 5 at different positions of each fibrous ring 24 are different, the fibrous ring 24 at different positions bears different tensile forces when the nucleus pulposus 16 is restricted from expanding, so that the anisotropy of the mechanical properties of the intervertebral disc is realized. The external morphology of the bionic intervertebral disc shows that the deformation degrees of the bionic intervertebral disc at different positions are different, so that the bionic intervertebral disc is matched with the physiological movement of the vertebrae more naturally after implantation of the bionic intervertebral disc.

The fibrous rings 24 include odd-numbered-layer fibrous rings 10 and even-numbered-layer fibrous rings 11. The number of the collagen fiber sheets 12 is 4 to 25. In the specific embodiment of the present disclosure, the number of the collagen fiber sheets 12 is 4, and the collagen fiber sheets 12 include the collagen fiber sheets 29 of the odd-numbered-layer fibrous rings and the collagen fiber sheets 30 of the even-numbered-layer fibrous rings.

The odd-numbered-layer fibrous rings 10 include collagen fiber sheets 29 of the odd-numbered-layer fibrous rings and the collagen fibers 31 of odd-numbered-layer fibrous rings. The collagen fibers 31 of odd-numbered-layer fibrous rings on the right side 20 of the sagittal plane are inclined counterclockwise from the bottom end thereof to the top end thereof, and the collagen fibers 31 of odd-numbered-layer fibrous rings on the left side 18 of the sagittal plane are inclined clockwise from the bottom end thereof to the top end thereof.

The even-numbered-layer fibrous rings 11 include the collagen fibers 30 of even-numbered-layer fibrous rings and the collagen fibers 32 of even-numbered-layer fibrous rings. The collagen fibers 32 of even-numbered-layer fibrous rings on the right side 20 of the sagittal plane are inclined clockwise from the bottom end thereof to the top end thereof, and the collagen fibers 32 of even-numbered-layer fibrous rings on the left side 18 of the sagittal plane are inclined counterclockwise from the bottom end thereof to the top end thereof.

Each of the inclination angles 23 is an included angle between a corresponding one of the collagen fibers 5 and a horizontal plane 28. An anterior inclination angle 22 of the inclination angles at the anterior part is 20 degrees, and a posterior inclination angle 21 of the inclination angles at the posterior part is 70 degrees. The inclination angles of the collagen fibers 5 are increased in turn from anterior to posterior, and the inclination angles of the collagen fiber 5 on the right side and the left side of the sagittal plane 19 of the bionic intervertebral disc are symmetrically distributed. The collagen fibers 5 at different positions of the collagen fiber sheets 12 are different in the inclination angles 23 and different in bearing tensile forces when the nucleus pulposus 16 is restricted from expanding, so that the anisotropy of the mechanical properties of the intervertebral disc is realized. During forward flexing of the bionic intervertebral disc (there is no other coupling motion in ideal states), a tensile force $F_{posterior\ collagen\ fibers}$ on the collagen fiber 5 of the odd-numbered-layer fibrous ring 10 of the posterior part 17 along a longitudinal direction of the collagen fiber is a product of a tensile force $F_{posterior}$ on the collagen fiber 5 which is perpendicular to the horizontal plane 28 and the sine of the inclination angle α° of the collagen fiber 5.

Namely, $F_{posterior\ collagen\ fibers}$ is equal to $F_{posterior}$ multiplied by sin α°. The tensile force $F_{posterior}$ collagen fibers on the collagen fiber 5 of the even-numbered-layer fibrous ring 11 of the posterior part 17 along the longitudinal direction of the collagen fiber is a product of the tensile force $F_{posterior}$ on the collagen fiber 5 which is perpendicular to the horizontal plane 28 and the sine of the inclination angle α° 23 of the collagen fiber 5. Namely, $F_{posterior\ collagen\ fibers}$ is equal to $F_{posterior}$ multiplied by sin α°. The tensile force on the collagen fiber 5 of the odd-numbered-layer fibrous ring 10 along the longitudinal direction of the collagen fiber is consistent with that on the collagen fiber 5 of the even-numbered-layer fibrous ring 11 along the longitudinal direction of the collagen fiber, represented by $F_{posterior\ collagen\ fibers}$, and the tensile force $F_{posterior}$ which is perpendicular to the horizontal plane is the value of the joint moment $M_{posterior}$ of the posterior part 17 divided by the force arm (the anterior-and-posterior distance of the bionic intervertebral disc is represented by D). During backward extending of the bionic intervertebral disc (there is no other coupling motion in ideal states), the tensile force $F_{anterior\ collagen\ fibers}$ on the collagen fiber 5 of the odd-numbered-layer fibrous ring 10 of the anterior part 9 along the longitudinal direction of the collagen fiber is a product of the tensile force $F_{anterior}$ on the collagen fiber 5 which is perpendicular to the horizontal plane 28 and the sine of the inclination angle α° 23 of the collagen fiber 5. Namely, $F_{anterior}$ collagen fibers is equal to $F_{anterior}$ multiplied by sin α°. The tensile force $F_{anterior\ collagen\ fibers}$ on the collagen fiber 5 of the even-numbered-layer fibrous ring 11 of the anterior part 9 along the longitudinal direction of the collagen fiber is a product of the tensile force $F_{anterior}$ on the collagen fiber 5 on the vertical horizontal plane 28 and the sine of the inclination angle α° 23 of the collagen fiber 5. Namely, $F_{anterior\ collagen\ fibers}$ is equal to $F_{anterior}$ multiplied by sin α°. The tensile force on the collagen fiber 5 of the odd-numbered-layer fibrous ring 10 along the longitudinal direction of the collagen fiber is consistent with that on the collagen fiber 5 of the even-numbered-layer fibrous ring 11 along the longitudinal direction of the collagen fiber, represented by $F_{anterior\ collagen\ fibers}$, and the tensile force $F_{anterior}$ which is perpendicular to horizontal plane 28 is the value of the joint moment $M_{anterior}$ of the anterior part 9 divided by the force arm (the anterior-and-anterior distance of the bionic intervertebral disc is represented by D). Literature research shows that the joint moment $M_{anterior}$ of the anterior part 9 is approximately equal to the joint moment $M_{posterior}$ of the posterior part 17, represented by M. Therefore, in the forward flexing and backward extending states, the tensile force F of the collagen fiber 5 of the anterior part 9 and the posterior part 17 along the longitudinal direction of the collagen fiber can be represented by F which is equal to M/D sin α°. The inclination angle 23 of the inclination angles at the anterior part 9 is 20 degrees, and the inclination angle 23 of the inclination angles at the posterior part 17 is 70 degrees. The tensile force $F_{anterior}$ of the collagen fiber 5 at the anterior part 9 along the longitudinal direction of the collagen fiber is equal to M/D×sin 20°, and the tensile force $F_{posterior}$ of the collagen fiber 5 of the posterior part 17 along the longitudinal direction of the collagen fiber is equal to M/D×sin 70°. Therefore, $F_{anterior}$ is less than $F_{posterior}$; namely the movement range of forward flexing is greater than the movement range of backward extending, which is consistent with the movement range data of a cadaver test. Similarly, in the ideal state of pure lateral bending, the inclination angles on the left side and the right side are equal, and the tensile forces of the collagen fibers on both sides of the intervertebral disc are equal, so the movement ranges of left lateral bending and right lateral bending in the cadaver test are basically equal. Similarly, the inclination angles 23 of the collagen fibers 5 in different areas of the bionic intervertebral disc are different, so the tensile forces of the collagen fibers 5 along the longitudinal direction of the collagen fiber are different, so that the mechanical anisotropy in different regions of the intervertebral disc is regulated.

The nucleus pulposus 16 is D-shaped, so that the stress area of the nucleus pulposus 16 can be increased, the stress is more uniformly applied on the nucleus pulposus 16, and local stress concentration is avoided. The upper end plate 3, the lower end plate 6 and the core 4 are D-shaped, which both match the shape of the human biological intervertebral disc. So, the integral stress is more uniform, and the supporting effect is better.

The surface of the upper end plate 3 is provided with an upper coating 2, the surface of the lower end plate 6 is provided with a lower coating 7, and the surfaces of the upper spikes 1 and the lower spikes 8 are also provided with coatings. The above coatings are all made of hydroxyapatite, undifferentiated mesenchymal cells can be induced to be differentiated into osteoblasts because of affinity interaction of the hydroxyapatite to bone tissues, and then the purpose of secondary fixation of the bionic intervertebral disc is achieved.

The upper end plate 3, the lower end plate 6, the upper spikes 1 and the lower spikes 8 are made of polyether ether ketone polymer which is high in hardness, so that the problem of prosthesis sinking caused by fractures of the upper end plate and the lower end plate can be avoided.

The nucleus pulposus 16 is made of an agarose hydrogel analogue. The stiffness of the nucleus pulposus 16 can be adjusted by changing the ratio of a base material to a curing agent, and appropriate load response can be achieved by the 10:1 ratio of the base material to the curing agent.

The collagen fiber sheets 12 are made of a polyurethane polymer material, and the collagen fibers 5 are made of a polyurethane polymer material.

The matrix layer 25 is made of a polyurethane polymer material. The elastic fibers 26 are made of a polyurethane polymer material.

What is claimed is:

1. A bionic intervertebral disc with mechanical anisotropy, comprising an upper end plate, a core and a lower end plate, wherein an upper end of the core is fixed on a lower surface of the upper end plate, and a lower end of the core is fixed on an upper surface of the lower end plate; an upper surface of the upper end plate is provided with upper spikes, and a lower surface of the lower end plate is provided with lower spikes;

the core comprises outer fibrous rings, a middle transition zone and an inner nucleus pulposus, the fibrous rings comprise collagen fiber sheets and collagen fibers, each of the collagen fibers is attached to a surface of a corresponding one of the collagen fiber sheets and arranged at an inclination angle, ones of the collagen fibers which are on every two adjacent layers of the collagen fiber sheets are arranged crosswise with each other, upper ends of the collagen fibers are tightly connected with the upper end plate, and lower ends of the collagen fibers are tightly connected with the lower end plate;

the collagen fibers are made of polymer materials with different elastic moduli, the elastic moduli of the collagen fibers from an anterior part of the bionic intervertebral disc to a posterior part of the bionic intervertebral disc are gradiently changed and gradually decreased, and the elastic moduli of ones, which are on a right side and a left side of an sagittal plane of the bionic intervertebral disc, of the collagen fibers are symmetrically distributed; and the transition zone comprises a matrix layer and elastic fibers, the elastic fibers are attached to a surface of the matrix layer, and the elastic fibers comprise coarse elastic fibers and fine elastic fibers;

wherein the fibrous rings comprise odd-numbered-layer fibrous rings and even-numbered-layer fibrous rings; a number of the collagen fiber sheets is 4 to 25, and the collagen fiber sheets comprise collagen fiber sheets of the odd-numbered-layer fibrous rings and collagen fiber sheets of the even-numbered-layer fibrous rings;

wherein the odd-numbered-layer fibrous rings comprise the collagen fiber sheets of the odd-numbered-layer fibrous rings and collagen fibers of the odd-numbered-layer fibrous rings, each of ones, which are on the right side of the sagittal plane, of the collagen fibers of odd-numbered-layer fibrous rings is inclined counterclockwise from a bottom end to a top end thereof, and each of ones, which are on the left side of the sagittal plane, of the collagen fiber of odd-numbered-layer fibrous rings is inclined clockwise from a bottom end to a top end thereof; and the even-numbered-layer fibrous rings comprise the collagen fiber sheets of the even-numbered-layer fibrous rings and collagen fibers of the even-numbered-layer fibrous rings, each of ones, which are on the right side of the sagittal plane, of the collagen fibers of the even-numbered-layer fibrous rings is inclined clockwise from a bottom end to a top end thereof, and each of ones, which are on the left side of the sagittal plane, of the collagen fibers of even-numbered-layer fibrous rings is inclined counterclockwise from a lower end to a top end thereof.

2. The bionic intervertebral disc with mechanical anisotropy according to claim 1, wherein the elastic fibers and the matrix layer of the transition zone form a honeycomb structure, and a honeycomb meshing size of a portion, which is located at a fibrous-ring transition zone, of the honeycomb structure is smaller and more compact, and a honeycomb meshing size of a portion, which is located at a nucleus pulposus transition zone, of the honeycomb structure is larger and sparser; and ones of the elastic fibers which are located in the anterior part have larger diameters than ones of the elastic fibers which are located in the posterior part, and the fine elastic fibers are interspersed among the coarse elastic fibers.

3. The bionic intervertebral disc with mechanical anisotropy according to claim 1, wherein each of the inclination angles is an included angle between a corresponding one of the collagen fibers and a horizontal plane, anterior inclination angles of the inclination angles which are at the anterior part are 20 degrees, posterior inclination angles of the inclination angles which are at the posterior part are 70 degrees, the inclination angles are gradually increased in turn from the anterior part to the posterior part, and ones of the inclination angles which are on the right side and the left side of the sagittal plane of the bionic intervertebral disc are symmetrically distributed.

4. The bionic intervertebral disc with mechanical anisotropy according to claim 1, wherein the upper end plate, the lower end plate, the upper spikes and the lower spikes are made of a polyether ether ketone polymer;

the nucleus pulposus is made of an agarose hydrogel analogue;

the collagen fiber sheets are made of a polyurethane polymer material, and the collagen fibers are made of the polyurethane polymer material;

the matrix layer is made of the polyurethane polymer material; and the elastic fibers are made of the polyurethane polymer material.

\* \* \* \* \*